(12) United States Patent
Esenaliev et al.

(10) Patent No.: US 9,167,993 B2
(45) Date of Patent: *Oct. 27, 2015

(54) NONINVASIVE GLUCOSE SENSING METHODS AND SYSTEMS

(76) Inventors: Rinat O. Esenaliev, League City, TX (US); Donald S. Prough, Galveston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/416,963

(22) Filed: Mar. 9, 2012

(65) Prior Publication Data

US 2012/0172686 A1    Jul. 5, 2012

Related U.S. Application Data

(63) Continuation of application No. 11/656,336, filed on Jan. 22, 2007, now Pat. No. 8,135,450.

(60) Provisional application No. 60/760,741, filed on Jan. 20, 2006.

(51) Int. Cl.
　　*A61B 5/145*　　(2006.01)
　　*A61B 5/00*　　(2006.01)
　　*A61B 5/107*　　(2006.01)

(52) U.S. Cl.
　　CPC ........... *A61B 5/14532* (2013.01); *A61B 5/0095* (2013.01); *A61B 5/1075* (2013.01)

(58) Field of Classification Search
　　CPC . A61B 5/1455; A61B 5/0095; A61B 5/14532
　　USPC .......................................... 600/316, 365, 438
　　See application file for complete search history.

(56) References Cited

U.S. PATENT DOCUMENTS

| | | | | |
|---|---|---|---|---|
| 5,119,819 A * | 6/1992 | Thomas et al. | ............... | 600/438 |
| 5,692,504 A * | 12/1997 | Essenpreis et al. | ........... | 600/316 |
| 6,567,678 B1 * | 5/2003 | Oosta et al. | .................... | 600/316 |
| 6,846,288 B2 * | 1/2005 | Nagar et al. | .................. | 600/316 |
| 6,954,662 B2 * | 10/2005 | Freger et al. | .................. | 600/316 |

* cited by examiner

*Primary Examiner* — Eric Winakur
(74) *Attorney, Agent, or Firm* — Robert W Strozier (57) ABSTRACT

New methods and systems for noninvasive glucose monitoring and sensing with electromagnetic waves or ultrasound are disclosed. The methods are based on absolute or relative measurement of tissue dimensions (or changes in the dimensions) including, but not limited to: thickness, length, width, diameter, curvature, roughness as well as time of flight of ultrasound and optical pulses and optical thickness, which change with changing blood glucose concentrations. By measuring noninvasively absolute or relative changes in at least one dimension of at least one tissue or tissue layer or absolute or relative changes in time of flight of ultrasound or optical pulses, one can monitor blood glucose concentration noninvasively.

23 Claims, 6 Drawing Sheets

FIG. 11

NONINVASIVE GLUCOSE SENSING METHODS AND SYSTEMS

RELATED APPLICATION

This application is a continuation of U.S. patent application Ser. No. 11/656,336 filed 22 Jan. 2007, now U.S. Pat. No. 8,134,450 issued 13 Mar. 2012, which claims priority to and the benefit of U.S. Provisional Patent Application Ser. No. 60/760,741, filed 20 Jan. 2006.

BACKGROUND OF THE INVENTION

1. Field of the Invention

The present invention relates to a method for noninvasive glucose sensing and a system for implementing the method.

More particularly, the present invention relates to a method for noninvasive glucose sensing including the step of measuring a thickness of a target tissue or a time of flight of ultrasound or optical pulses in the target tissue and determining a glucose value from the thickness of the target tissue or the time of flight in the target tissue in accordance with a target tissue thickness or time of flight versus glucose calibration curve and a system for implementing the method.

2. Description of the Related Art

Other techniques can be used for tissue dimension measurement. Near infrared absorption spectroscopy can provide tissue thickness measurement (U.S. Pat. No. 6,671,542). However, techniques with higher resolution are needed for accurate glucose monitoring. One can use optical refractometry (U.S. Pat. No. 6,442,410) for noninvasive blood glucose measurement. However, this technique has limitations associated with low accuracy and specificity of glucose monitoring.

U.S. Pat. No. 7,039,446 B2 discloses a variety of techniques for analyte measurements but does not disclose how to measure tissue thickness and use the thickness measurements for glucose concentration monitoring. Acoustic velocity measurement in blood was proposed in U.S. Pat. No. 5,119,819 for glucose monitoring. However, tissue thickness measurements were not disclosed. Photoacoustic techniques were proposed in U.S. Pat. No. 6,846,288 B2 for measurement of blood glucose concentration by generating photoacoustic waves in blood vessels.

These and other techniques proposed for noninvasive glucose monitoring have limited accuracy and specificity.

Thus, there is still a need in the art for simple noninvasive glucose sensing methods and systems.

SUMMARY OF THE INVENTION

The present invention provides a blood glucose monitoring technique that is critically important for diabetic patients. Tight glucose control decreases dramatically complications and mortality associated with diabetes. Blood glucose monitoring is an important part of blood glucose control. At present, all techniques for blood glucose monitoring are invasive and require a drop of blood or interstitial fluid for measurement.

The present invention also provides a noninvasive blood glucose monitoring technique that would also be invaluable in critically ill patients, regardless of whether those patients are diabetic. Clinical studies clearly establish that morbidity and mortality are reduced in patients requiring intensive care if blood glucose is tightly controlled between 80 and 110 mg/dL (Van den Berghe G, 2005; Vanhorebeek I, 2005; van den Berghe G, 2001). However, conventional techniques for tightly controlling blood glucose have several limitations, including the need for frequent blood sampling and the risk that insulin administration will induce hypoglycemia (blood glucose <60 mg/dL) between sampling intervals and that hypoglycemia therefore will not be promptly diagnosed and treated. A continuous method of monitoring blood glucose by measuring tissue thickness would greatly improve the ease and safety of tightly controlling blood glucose with insulin in critically ill patients.

The measurement of dimensions or time of flight can be performed in a variety of tissues including, but not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue. The dimension(s) of these tissues can change with blood glucose concentration. For instance, our studies demonstrated that increase of blood glucose concentration may decrease the thickness (and optical thickness) of and time of flight of ultrasound pulses in the skin tissues (namely, dermis). Measurements of dimensions of specific tissue layers (within one of these tissues) can be used for glucose monitoring. Measurement of one, two or more dimensions can be performed for more accurate, specific, and sensitive glucose monitoring. Ratios of dimensions of two or more tissues can be used for more robust, accurate, specific, and sensitive glucose monitoring. For instance, increasing blood glucose concentration may increase lens thickness and decrease anterior chamber thickness (Furushima et al., 1999). The ratio of these changes may provide robust, accurate, and sensitive blood glucose monitoring. One can use measurement of total dimensions of complex tissues consisting of two or more different tissues. Measurement of time of flight of ultrasound or optical waves in these tissues, or optical thickness of these tissues can also be used for non-invasive glucose monitoring without calculating or determining geometrical thickness or other dimensions of these tissues.

BRIEF DESCRIPTION OF THE DRAWINGS

The invention can be better understood with reference to the following detailed description together with the appended illustrative drawings in which like elements are numbered the same:

A short radiofrequency (typically nanosecond) pulse can be used instead of the optical pulse to generate the ultrasound waves.

FIG. 11 depicts an optical system for generating short, broad-band ultrasound pulses in an optically absorbing medium. The medium is attached to the tissue surface. The optical system produces at least one short (typically nanosecond or picosecond) optical pulse and directs it on the absorbing medium. The energy of the optical pulse is absorbed by the medium that results in generation of a short ultrasound (acoustic) pulse. The ultrasound pulse then propagates in the tissue and is reflected from tissue layers. An ultrasound transducer detects the reflected ultrasound pulses and a processor analyzes the signal from the transducer and calculates the time of flight of the ultrasound pulses and glucose concentration. A short (typically nanosecond) radiofrequency electromagnetic pulse can be used instead of the short optical pulse to generate a short, broad-band ultrasound pulse in a radiofrequency absorbing medium.

DETAILED DESCRIPTION OF THE INVENTION

The invention discloses method and apparatus for noninvasive glucose monitoring and sensing with electromagnetic (including optical) waves or ultrasound. This method is based on absolute or relative measurement of tissue dimensions (or changes in the dimensions) including, but not limited to: thickness, length, width, diameter, curvature, roughness as well as optical thickness and time of flight of optical or ultrasound pulses. Changes in blood glucose concentration may increase or decrease tissue dimensions due to a variety of possible mechanisms. One of them is the glucose-induced osmotic effect. The osmotic effect may decrease or increase tissue dimension(s) depending on tissue type, structure, location, condition, cell density, blood content, and vascularization. By measuring noninvasively absolute or relative changes in at least one dimension of at least one tissue or tissue layer, one can monitor blood glucose concentration noninvasively. Variation of glucose concentration may also change sound velocity and refractive index. Thus, the measurement of time of flight of the ultrasound or optical pulses may provide more robust, accurate, and specific monitoring of blood glucose concentration compared to geometrical dimension measurements.

Tissues include, but are not limited to: skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue. The dimension(s) of these tissues can change with blood glucose concentration. For instance, our studies demonstrated that increase of blood glucose concentration may decrease the time of flight in and thickness of the skin tissues (namely, dermis). Measurements of dimensions of specific tissue layers (within one of these tissues) can be used for glucose monitoring. Measurement of one, two or more dimensions can be performed for more accurate, specific, and sensitive glucose monitoring. Ratio of dimensions of two or more tissues can be used for more robust, accurate, specific, and sensitive glucose monitoring. For instance, increase of blood glucose concentration may increase lens thickness and decrease anterior chamber thickness (Furushima et al., 1999). The ratio of these changes may provide robust, accurate, and sensitive blood glucose monitoring. One can use measurement of total dimensions of complex tissues consisting on two or more different tissues. Measurement of optical thickness of these tissues can also be used for non-invasive glucose monitoring.

The electromagnetic wave or ultrasound with at least one wavelength (frequency) is directed to the tissue or tissue layer. Reflected, refracted, transmitted, scattered, backscattered, or forward-scattered waves can be used for measurement of the tissue dimensions. The measurements of tissue dimensions can be performed in the reflection mode or in the transmission mode. In the reflection mode, irradiation and detection are performed from one side. In the transmission mode, irradiation and detection are performed from different sides.

The electromagnetic waves include optical radiation (near infrared, infrared, far infrared, visible, and UV light in the wavelength range from about 200 nanometers to about 100 microns), terahertz waves, microwaves, radiowaves, low-frequency waves, static electric or magnetic filed. A combination of different waves can be used with one, two, or multiple wavelengths (frequencies) can be used for more accurate, specific, and sensitive glucose monitoring.

Ultrasound includes ultrasonic waves in the frequency range from about 20 kHz to about 10 Gigahertz. One, two, or multiple frequencies or broad-band ultrasound pulses can be used for more accurate, specific, and sensitive glucose monitoring. The broad-band ultrasound pulses can be generated by using short electromagnetic pulses irradiating a strongly absorbing medium attached to the tissue. Short optical pulses induced by laser and non-laser sources can be used for generation of the broad-band ultrasound pulses.

Combination of electromagnetic waves and ultrasound may provide higher accuracy and specificity of glucose monitoring. Hybrid techniques such as optoacoustics and thermoacoustics can be used for tissue dimension or time of flight measurement. Short optical pulses from laser or non-laser sources or short radiofrequency pulses can be used for generating acoustic waves in the tissue. Acoustic (ultrasound) detectors, preferably, broad-band detectors can be used for detection of the acoustic waves. The time of flight (and glucose-induced signal shift) can be measured by analyzing the optoacoustic and thermoacoustic waves. One can calculate tissue thickness, L, by using the formula: L=ct, where c is the speed of sound in tissue. In contrast to the formula presented above for the pure ultrasound technique, the factor of ½ is not used because the optoacoustic or thermoacoustic waves propagate only one way (from tissue to detector). For additional information on optoacoustics the reader is referred to U.S. Pat. Nos. 6,751,490, and 6,498,942, incorporated herein by reference.

The electromagnetic waves and ultrasound can be pulsed, continuous wave, or modulated. Amplitude and/or frequency can be modulated to provide high signal-to-noise ratio.

The measurements can be performed with one or more (array) of detectors of electromagnetic or ultrasound waves. One can use multiple sources of electromagnetic waves or ultrasound for glucose monitoring.

Combination of these techniques with other techniques may provide more accurate, specific, and sensitive glucose monitoring.

The glucose sensing device can be wearable to provide continuous monitoring. A wearable device (like a wrist watch) can be used for continuous skin thickness measurement. One can use specially-designed glasses for glucose monitoring systems based on eye tissue thickness or time of flight measurement.

The glucose-sensing probe(s) attached to the tissue can be controlled by a radiofrequency controller remotely to minimize patient's discomfort. Light-weight probes can be used to decrease pressure applied by the probe on the tissue surface and improve accuracy of glucose monitoring.

The tissue temperature should be stabilized and be, preferably, in the range from about 37° C. to about 40° C. A temperature controller with a heater should be used to provide a stable temperature in this range. The stable temperature yields constant speed of sound and refractive index, and therefore, more accurate and specific glucose monitoring. Moreover, tissue warming to these temperatures improves blood flow and glucose transport in the tissues that yield to more accurate and specific glucose monitoring.

General Information

The inventors disclose monitoring blood glucose concentration noninvasively by measuring absolute or relative tissue dimensions (or changes in the dimensions) including, but not limited to: thickness, length, width, diameter, curvature, roughness as well as time of flight of ultrasound and electromagnetic pulses and optical thickness. The inventors disclose the use of electromagnetic or ultrasound techniques for tissue dimension measurement and, in particular, time of flight techniques based on generation of short and ultrashort ultrasound or electromagnetic pulses, focused light reflection technique and focus-detection technique for noninvasive measurement of tissue thickness as well as other techniques based on detection of reflected, refracted, transmitted, scattered, backscattered, or forward-scattered wave. The inventors have demonstrated in vivo that time of flight of ultrasound pulses in skin and skin thickness decrease with blood glucose concentration. The inventors disclose the use of measurement of time of flight and dimensions of skin tissues (dermis, epidermis, subcutaneous fat), eye tissues (lens, anterior chamber, vitreous cavity, eye ball, sclera), mucosal tissues, nailbed, lunula, connective tissue, muscle tissue, blood vessels, cartilage tissue, tendon tissue for noninvasive glucose monitoring. The inventors disclose the use of optoacoustic and thermoacoustic techniques for tissue time of flight and dimension measurements. The inventors disclose the use of time of flight changes (signal shift) and ratio of dimensions (or changes in dimensions) of different tissues for more accurate glucose monitoring. The inventors disclose the use of two or more wavelengths (frequencies) for more accurate glucose monitoring. The inventors disclose the use of broad-band ultrasound pulses generated by optical pulses in optically-absorbing media or generated by radiofrequency pulses in radiofrequency absorbing media. The inventors disclose the use of time-resolved techniques based on reflection of ultrashort optical pulses from tissue layers and interfaces. The inventors also disclose the use of this technique for noninvasive blood glucose monitoring in critically ill patients, regardless of whether those patients are diabetic. Clinical studies clearly establish that morbidity and mortality is reduced in patients requiring intensive care if blood glucose is tightly controlled between 80 and 110 mg/dL (Van den Berghe G, 2005; Vanhorebeek I, 2005; van den Berghe G, 2001). However, conventional techniques for tightly controlling blood glucose have several limitations, including the need for frequent blood sampling and the risk that insulin will induce hypoglycemia between sampling intervals and that hypoglycemia will not be promptly diagnosed and treated. A continuous method of monitoring blood glucose by measuring skin thickness or time of flight would greatly improve the ease and safety of tightly controlling blood glucose with insulin therapy in critically ill patients.

The inventors also disclose the use of combined measurement of time of flight of ultrasound or optical pulses with measurement of attenuation, phase, and frequency spectrum of the ultrasound or optical pulses reflected from the tissues to improve accuracy and specificity of glucose monitoring. The attenuation can be measured by analyzing the amplitude of the reflected pulses. The phase and the frequency spectrum can be measured by analyzing the temporal characteristics of the reflected pulses. The amplitude (attenuation), phase, and frequency of the reflected pulses may vary with glucose concentration. Measurement of these parameters or glucose-induced changes in these parameters may provide additional information which combined with the time of flight measurements can be used for more accurate and specific glucose monitoring.

Blood glucose monitoring is critically important for diabetic patients. Tight glucose control decreases dramatically complications and mortality associated with diabetes. Blood glucose monitoring is an important part of blood glucose control. At present, all techniques for blood glucose monitoring are invasive and require a drop of blood or interstitial fluid for measurement.

There are no techniques for noninvasive glucose monitoring on the market. The disclosed technique is novel because glucose-induced changes in tissue dimensions or time of flight have not been studied yet. This invention is not obvious to a person having ordinary skill in the art to which this invention pertains. It is necessary to understand and demonstrate why and how changes in blood glucose concentration decrease or increase tissue dimensions or time of flight of ultrasound or optical pulses.

The broadest application is noninvasive blood glucose monitoring in diabetic patients. However, continuous monitoring of blood glucose in critically ill patients would contribute a separate, clinically invaluable tool in patients who are not diabetic.

The noninvasive glucose monitoring of this invention can be performed by using a variety of techniques. The following examples are shown to demonstrate possible approaches to glucose monitoring by using dimension or time of flight measurements with different techniques in various tissues.

Figure 1:
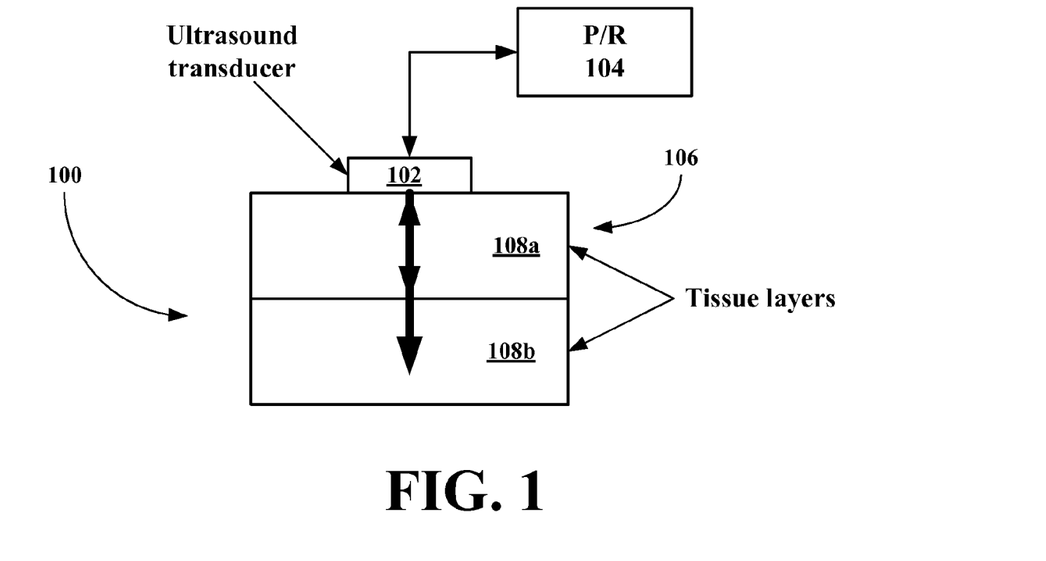
FIG. 1 depicts an embodiment of an ultrasound system for tissue thickness or ultrasound time of flight measurement.

Referring now to FIG. 1, an embodiment of a system of this invention, generally 100, is shown to include an ultrasound transducer 102 in electrical communication or connected electronically or electrically to a pulser/receiver (P/R) 104. The P/R 104 generates at least one electrical pulse which is converted into an ultrasound pulse by the transducer 102. The ultrasound pulse propagates in a tissue 106 and is reflected from tissue layers 108a&b due to an acoustic impedance difference (mismatch) between the layers 108a&b. The reflected ultrasound pulses are detected by the transducer 102 and analyzed by the P/R 104 to calculate the time of flight or thickness of the layers 108a&b. The time of flight or thickness (or their changes) is then converted into glucose concentration or changes in glucose concentration by using a processor and glucose concentration is displayed by a display. The processor and display can be incorporated in the pulser/receiver in one casing or connected to the pulser/receiver using wires or using wireless radiofrequency communication.

Figure 2:
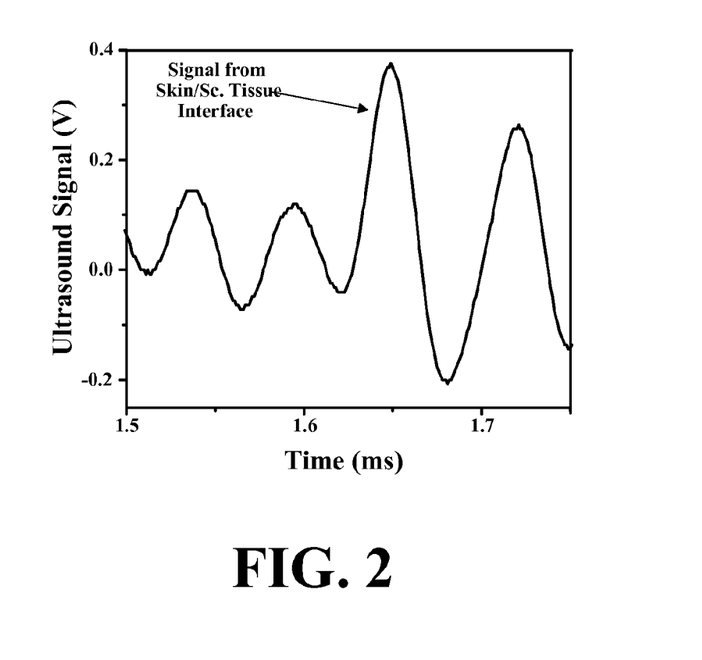
FIG. 2 depicts a typical ultrasound signal from the skin/subcutaneous tissue interface from a human subject (forearm area) recorded by the system of this invention.

Referring now to FIG. 2, a 20-MHz non-focused piezoelectric transducer was used to generate short ultrasound pulses. The signal is resulted from acoustic impedance mismatch between the skin and subcutaneous tissue. The time of flight of the ultrasound pulses from the upper skin surface to the skin/subcutaneous tissue interface and back, t, is equal to 1.65 μs (microsecond). This time of flight varies with glucose concentration. Glucose-induced changes in skin result in temporal shift of the signal, Δt, due to the changes in the time of flight. By measuring the signal shift one can monitor glucose concentration. This can be done without calculating the geometrical thickness of the skin (or any other tissue). Thus, the system can monitor glucose concentration by measuring the time of flight of the ultrasound pulses (waves) t or changes in the time of light Δt. One can calculate skin thickness, L, by using the formula: $L=ct/2$, where c is the speed of sound in skin and factor of ½ is due to the propagation of the ultrasound pulse from the skin surface to the interface and back. The skin thickness measured with this system is equal to $L=1.5$ mm/μs×1.65 μs/2=1.24 mm assuming that c=1.5 mm/μs (typical speed of sound in soft tissues).

Figure 3:
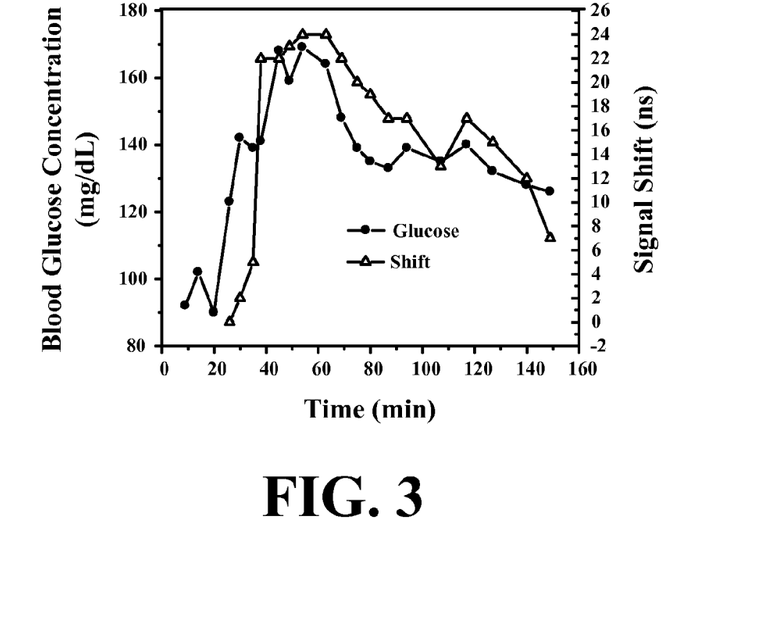
FIG. 3 shows blood glucose concentration (solid circles) in a human subject before and after a sugar drink at the $20^{th}$ minute (76 g of sugar in 650 mL of water).
Figure 4:
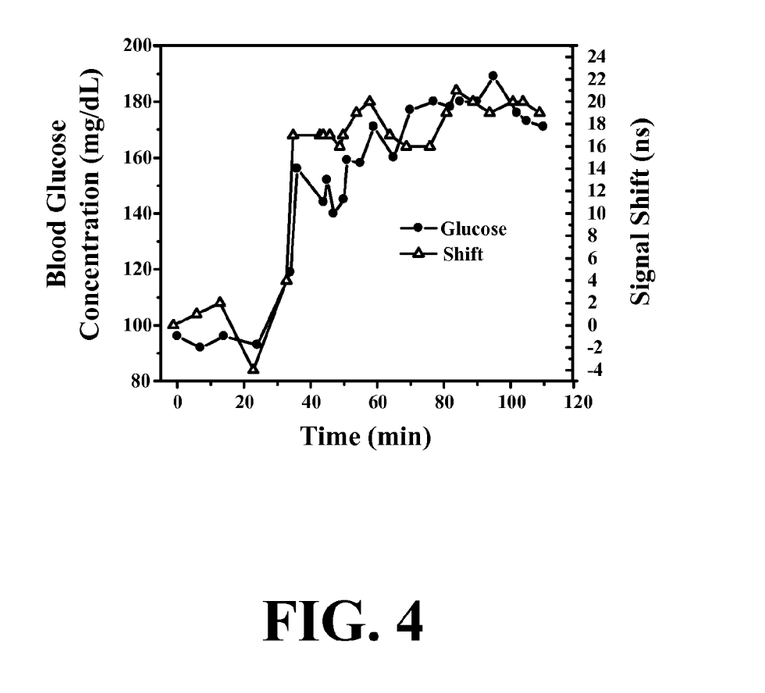
FIG. 4 depicts similar in vivo results before and after a higher glucose load (108 g of sugar in 1 L of water) at $25^{th}$ minute. The measurements were performed with the same ultrasound system from the subject's forearm. The data show good correlation of the signal shift (and, therefore, time of flight of ultrasound pulses in the skin) with blood glucose concentration.

Referring now to FIGS. 3 and 4, blood glucose concentration was measured with a standard invasive technique involving blood sampling from finger tips with a lancet. The ultrasound system shown in FIG. 1 was used to measure time of flight of ultrasound waves in skin t and changes in the time of flight Δt (the signal shift). The transducer was attached to the subject's forearm and detected continuously the ultrasound pulses reflected from the skin/subcutaneous tissue interface. The shift of the signals recorded at the time of blood sampling (and, therefore, the time of flight of ultrasound pulses in the skin) closely follows blood glucose concentration. The time of flight decreased with increase of blood glucose concentration. The positive signal shift plotted in the graph corresponds to decrease of the time of flight, while negative values of the signal shift correspond to increase of the time of flight.

Figure 5:
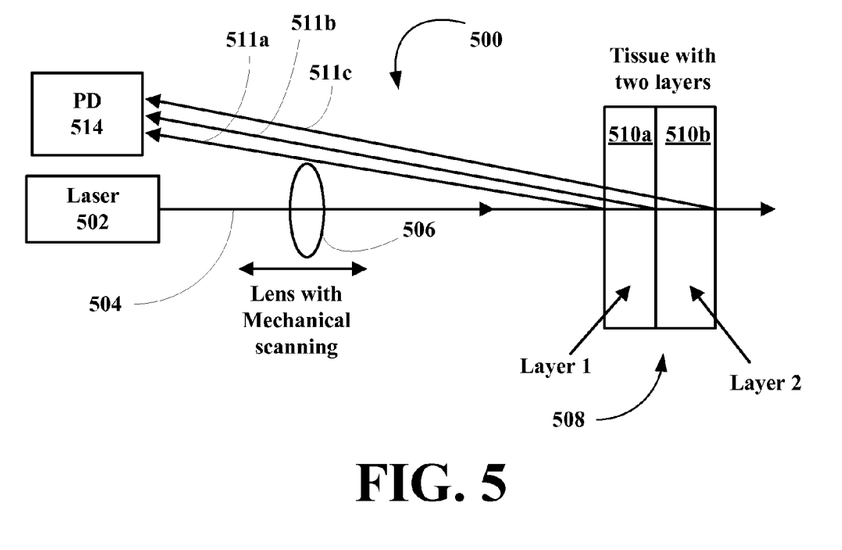
FIG. 5 depicts an embodiment of an optical system for noninvasive glucose monitoring using tissue thickness measurement by a focusing lens with in-depth mechanical scanning. Light from a laser or other optical source is focused on the tissue layers. When focus position coincides with tissue boundary, a peak of reflection is induced and is recorded by a photodetector (PD).

Referring now to FIG. 5, another embodiment of a system of this invention, generally 500, is shown to include an is shown to include a pulsed laser light source 502, which produces a pulse beam 504. The pulsed beam 504 passes through a mechanically scanning lens 506 and impinges on a tissue site 508 having layers 510a&b. When focus position coincides with a tissue boundary, a peaks of reflection 512a-c is induced and is recorded by a photodetector (PD) 514.

Figure 6:
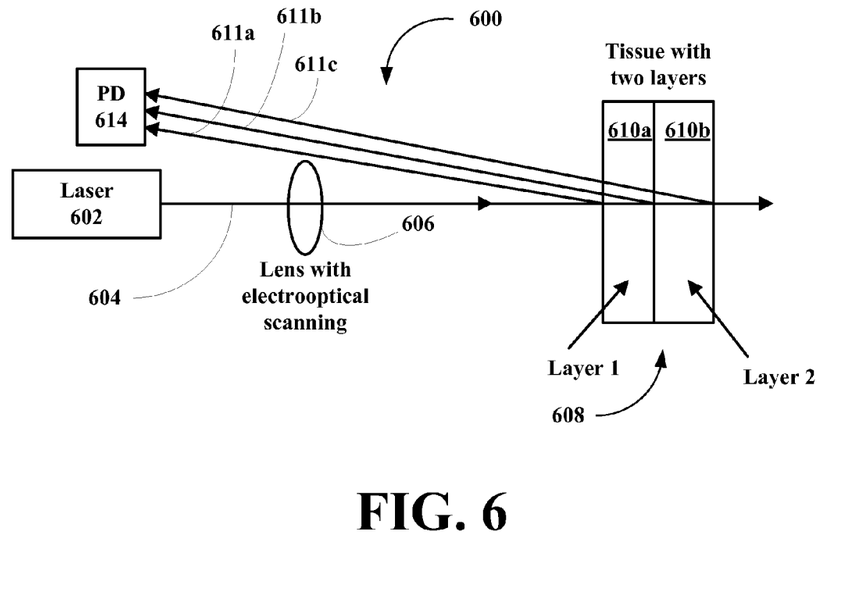
FIG. 6 depicts an optical system for noninvasive glucose monitoring using tissue thickness measurement by a focusing lens with in-depth electrooptical scanning. Light from a laser or other optical source is focused on the tissue layers. When focus position coincides with tissue boundary, a peak of reflection is induced and is recorded by a photodetector (PD).

Referring now to FIG. 6, another embodiment of a system of this invention, generally 600, is shown to include a pulsed laser light source 602, which produces a pulsed beam 604. The pulsed beam 604 passes through a focusing with in-depth electrooptical scanning lens 606 and impinges on a tissue site 608 having layers 610a&b. When focus position coincides with a tissue boundary, peaks of reflection 612a-c is induced and is recorded by a photodetector (PD) 614.

Figure 7:
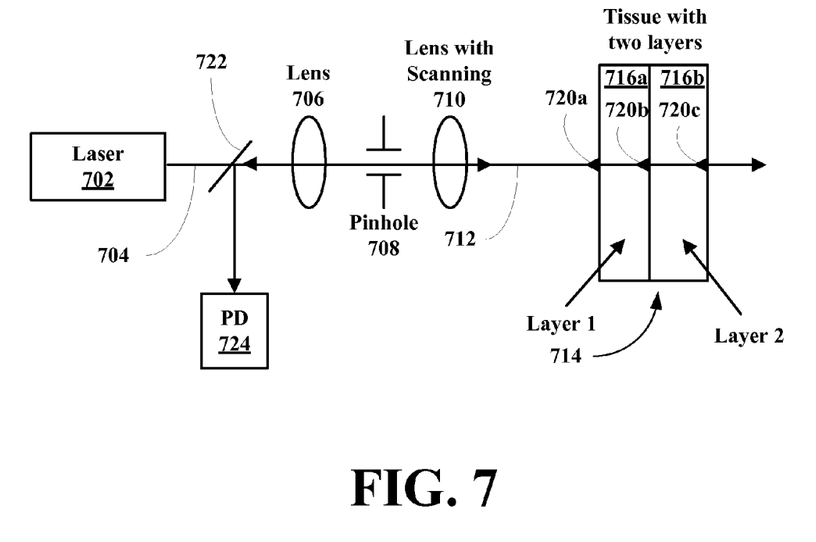
FIG. 7 depicts an optical system for noninvasive glucose monitoring using tissue thickness measurement with a pinhole and a focusing lens with scanning. Light from a laser or other optical source is focused through the pinhole on tissue layers. When focus position coincides with tissue boundary, a peak of reflection is induced and is recorded by a photodetector (PD) through the pinhole.

Referring now to FIG. 7, another embodiment of a system of this invention, generally 700, is shown to include a pulsed laser light source 702, which produces a pulsed beam 704. The pulsed beam 704 passes through a first lens 706, then through a pinhole 708; and finally, through a focusing with in-depth electrooptical scanning lens 710. The focused beam 712 then impinges on a tissue site 714 having layers 716a&b. When focus position coincides with a tissue boundary, peaks of reflection 720a-c is induced at each boundary. The reflects come back through the scanning lens 710, then the pinhole 708, then the first lens 706 to a dichromic 722 to a photodetector (PD) 724, where is the reflected beam is record and analyzed.

Figure 8:
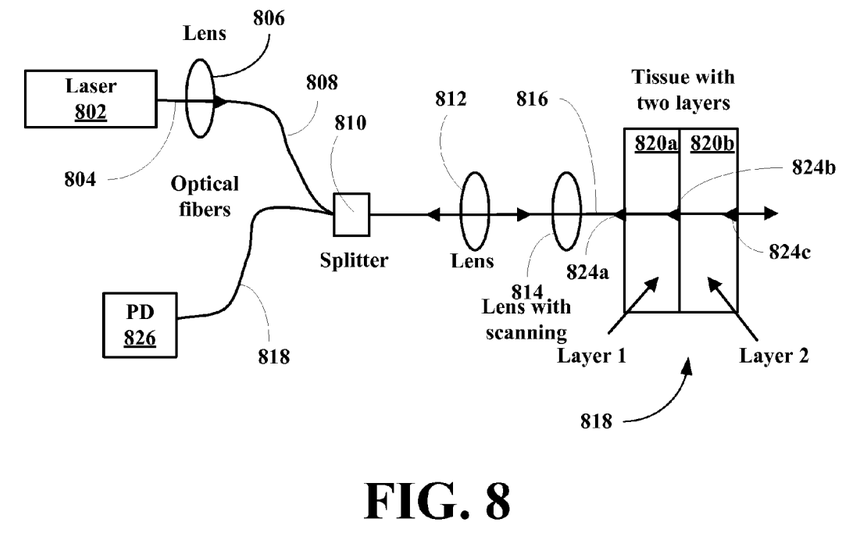
FIG. 8 depicts an optical system for noninvasive glucose monitoring using tissue thickness measurement with a fiber-optic system and a focusing lens with scanning. Light from a laser or other optical source is focused through the fiber-optic system on tissue layers. When focus position coincides with tissue boundary, a peak of reflection is induced and is recorded by a photodetector (PD) through the fibers.

Referring now to FIG. 8, another embodiment of a system of this invention, generally 800, is shown to include a pulsed laser light source 802, which produces a pulsed beam 804. The pulsed beam 804 passes through a first lens 806, then into a fiber optics fiber 808 and then into a splitter 810. After exiting the splitter 810, the beam 804 proceeds through a second lens 812 and then through a focusing with in-depth electrooptical scanning lens 814. The focused beam 816 then impinges on a tissue site 818 having layers 820a&b. When focus position coincides with a tissue boundary, peaks of reflection 824a-c is induced at each boundary. The reflects come back through the scanning lens 814, then the second lens 812 to the beam splitter 810 to a photodetector (PD) 826, where is the reflected beam is record and analyzed.

EXPERIMENTAL SECTION OF THE INVENTION

Example 1

Glucose-induced changes in skin thickness or time of flight measured with electromagnetic techniques.

Glucose-induced changes in skin tissue thickness (optical thickness) can be measured by using electromagnetic waves including, but not limited to: optical radiation, terahertz radiation, microwaves, radiofrequency waves. Optical techniques include but not limited to reflection, focused reflection, refraction, scattering, polarization, transmission, confocal, interferometric, low-coherence, low-coherence interferometry techniques.

A wearable, like a wrist watch, optical-based glucose sensor can be developed.

Example 2

Glucose-induced changes in time of flight in and thickness of skin measured with ultrasound techniques.

Glucose-induced changes in skin tissue thickness and time of flight can be measured by using ultrasound waves in the frequency range from 20 kHz to 10 Gigahertz. These techniques include but not limited to reflection, focused reflection, refraction, scattering, transmission, confocal techniques. It is well known that by using high frequency ultrasound can provide high-resolution images of tissues.

One can use ultrasound frequencies higher than 10 MHz for measurement of skin thickness and time of flight.

FIGS. 1 to 4 show the system, the typical signal from skin/subcutaneous tissue interface, and glucose-induced signal shift (changes in time of flight) measured by the system. A wearable, like a wrist watch, ultrasound-based glucose sensor can be developed.

Example 3

Glucose-induced changes in skin thickness and time of flight measured with optoacoustics or thermoacoustic techniques.

Figure 10:
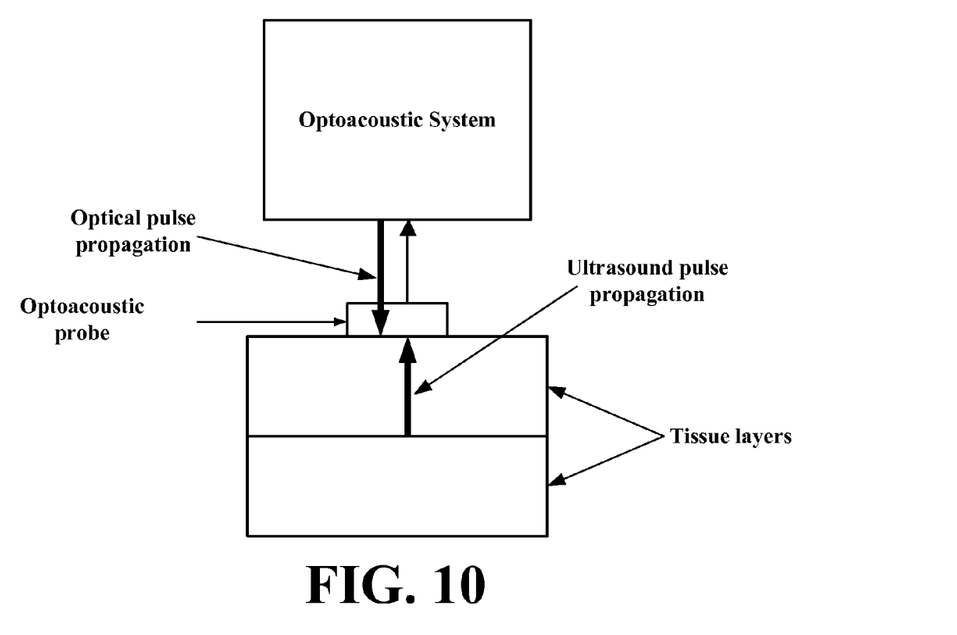
FIG. 10 depicts an optoacoustic system for time of flight or thickness measurements. At least one short (typically nanosecond or picosecond) optical pulse is generated by the system, directed to the tissue, generates ultrasound waves in the tissues. An ultrasound transducer detects the ultrasound waves and the ultrasound signal is analyzed by a processor. The optically-induced ultrasound waves carry information on the ultrasound time of flight in tissue layers. The geometrical thickness can be calculated by multiplying the time of flight by speed of sound.

Glucose-induced changes in skin tissue thickness and time of flight can be measured by using optoacoustic or thermoacoustic techniques which may provide accurate tissue dimension measurement when short electromagnetic (optical or microwave) pulses are used in combination with wide-band ultrasound detection. FIG. 10 shows such a system.

Optical detection of the ultrasound waves can be used instead of the ultrasound transducer.

Example 4

Glucose-induced changes in the lens and anterior chamber thickness measured with optical techniques.

One can use measurement of eye tissue thickness (including optical thickness) with optical techniques for noninvasive and accurate glucose monitoring. The preferred embodiment is glucose monitoring by measuring thickness of the lens and/or anterior chamber or their ratio by using non-contact reflection techniques, preferably with focused light reflection technique. The focused reflection technique utilizes focused light for tissue irradiation and detection of reflection peaks (maxima) when the light is focused on tissue surfaces. If the focus is scanned in depth, one can measure tissue thickness by recording and analyzing the peaks of reflections during the scanning. This technique allows for measurement of tissue thickness with high (submicron) accuracy. One can use multiple detectors to increase signal-to-noise ratio and, therefore, accuracy of glucose monitoring. This technique can be used for tissue thickness measurement (as well as optical thickness measurements) in other tissues (not only eye tissues).

The focused light reflection technique in its simplest form can utilize a light beam focused with a lens on a tissue surface and detection of the reflected light with at least one optical detector positioned at a small angle with respect to the incident beam. By in-depth scanning the focus, one can detect peaks of reflected light intensity when the focus reaches a tissue surface, or a tissue layer surface. FIG. 5 shows such a system which utilizes a lens with mechanical scanning. One can use a lens with electrooptical scanning that provides fast in-depth scanning and with no moving parts (FIG. 6). A voltage is applied to the lens to vary the focus position within the tissue by using electrooptical effects.

Another modification of this technique is to use a pinhole that may provide higher signal-to-noise ratio by reducing stray light and background tissue scattering light (FIG. 7). Instead of a pinhole one can use a fiber-optic system (FIG. 8) that may provide high signal-to-noise ratio too. Similar fiber-optic system was used by Zeibarth et al. It was demonstrated that such a system can measure eye tissue thickness (including the lens) with high (submicron) accuracy (Zeibarth et al.).

Furushima et al. demonstrated using ultrasound techniques (with submillimeter resolution) that the thickness of the lens increases, while thickness of anterior chamber decreases with blood glucose concentration. Therefore, one can monitor noninvasively glucose concentration with high accuracy and sensitivity by using the measurement of lens and anterior chamber thickness with either the focused light reflection technique or the focus-detection technique. The system (either the focused light reflection system or the focus-detection system) can be assembled on glasses or other wearable device to provide convenient and continuous measurement.

Example 5

Glucose-induced changes in the lens and anterior chamber thickness measured with ultrasound techniques.

High frequency ultrasound (>10 MHz) can be used for glucose monitoring based on measurement of the lens and/or anterior chamber thickness or time of flight in these tissues. Focused reflection technique utilizing focused ultrasound can be applied too to provide higher resolution.

Example 6

Glucose-induced changes in the skin or lens and anterior chamber thickness or time of flight measured with optoacoustic or thermoacoustic techniques (FIG. 10).

The optoacoustic and thermoacoustic techniques can provide acceptable accuracy of the thickness or time of flight measurement in these tissues if short optical (or microwave, or radiofrequency) pulse are used for generation of the thermoelastic waves and if detection of these waves is performed with wide-band, high-frequency ultrasound detectors. Focused radiation can be used to provide better accuracy of measurement.

Optical detection of the optoacoustic or the thermoelastic waves can be used to provide non-contact measurement of the optoacoustic and the thermoelastic waves. The non-contact optical detection is more preferable for detecting these waves induced in the eye tissues compared to detection by ultrasound transducers because it minimizes discomfort for the patient.

Example 7

Figure 9:
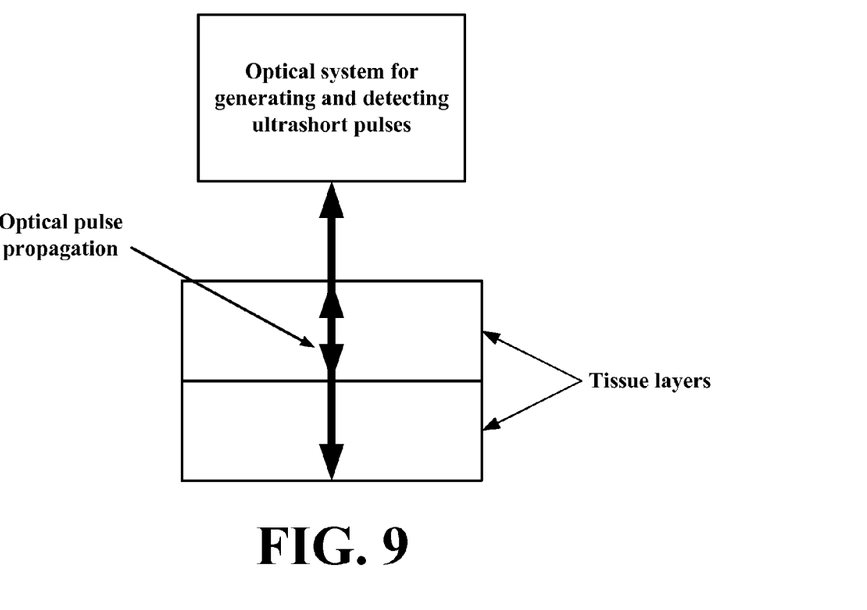
FIG. 9 depicts a time-resolved optical system generating ultrashort (typically femtosecond) optical pulses, directing the pulses to the tissues, and detecting the pulses reflected from tissue layers. The system measures the time of flight of the optical pulses and converts them into blood glucose concentration.

A time-resolved optical system (FIG. 9) can be used for glucose monitoring in the tissues, preferably the tissues of the eye. The system generates ultrashort (typically femtosecond) optical pulses, directs the pulses to the tissues, and detects the pulses reflected from tissue layers. The system measures the time of flight of the optical pulses and converts them into blood glucose concentration.

Example 8

An optical system for generating short, broad-band ultrasound pulses in an optically absorbing medium (FIG. 11) can be used for glucose monitoring. The medium is attached to the skin surface. The optical system produces at least one short (typically nanosecond or picosecond) optical pulse and directs it on the absorbing medium. The energy of the optical pulse is absorbed by the medium that results in generation of a short ultrasound (acoustic) pulse. The ultrasound pulse then propagates in the tissue and is reflected from tissue layers. An ultrasound transducer detects the reflected ultrasound pulses and a processor analyzes the signal from the transducer and calculates the time of flight of the ultrasound pulses and glucose concentration.

Figure 11:
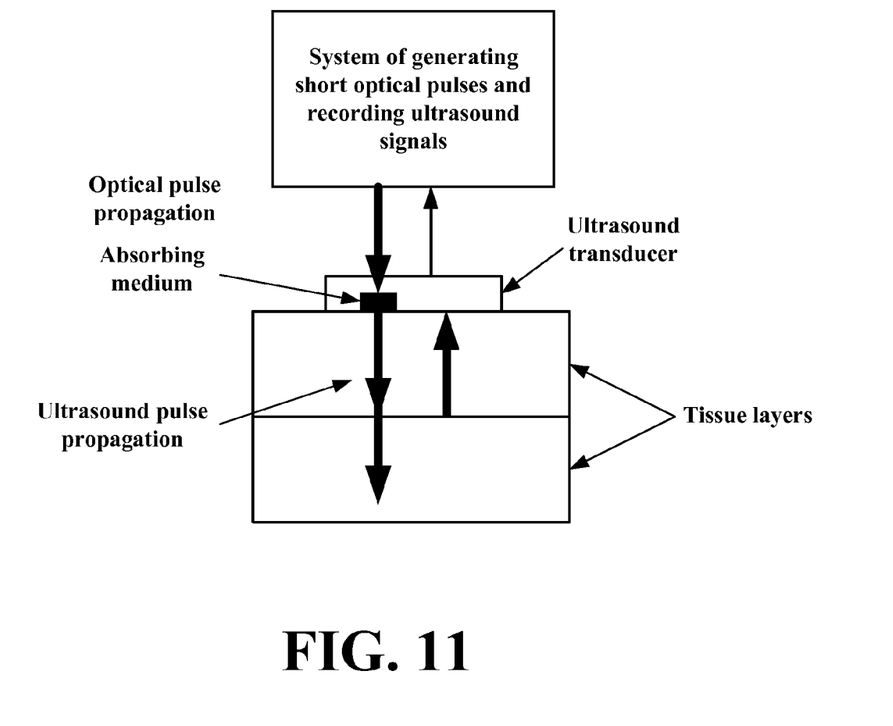

A short (typically nanosecond) radiofrequency electromagnetic pulse can be used instead of the short optical pulse to generate a short, broad-band ultrasound pulse in a radiofrequency absorbing medium.

An optical detection of the reflected ultrasound pulses can be used.

The existing techniques for glucose monitoring are invasive. For last 20 years many noninvasive glucose monitoring techniques have been proposed, however they suffer from insufficient accuracy, sensitivity, and specificity. At present, there is no noninvasive glucose monitor on the market.

The methods of the present invention can be practiced so that the measurements include attenuation, phase, and frequency of the reflected and incident beams or beam pulses.

REFERENCES CITED IN THE INVENTION

Ziebarth N., Manns F., Parel J.-M. Fibre-optic focus detection system for non-contact, high resolution thickness measurement of transparent tissues. Journal of Physics D: Applied Physics, 2005, v. 38, pp 2708-2715.

Furushuma M., Imazumi M., Nakatsuka K. Changes in Refraction Caused by Induction of Acute Hyperglycemia in Healthy Volunteers. Japanese Journal of Ophthalmology, 1999, v 43, pp 398-403.

Van den Berghe G, Schoonheydt K, Becx P, Bruyninckx F, Wouters P J. Insulin therapy protects the central and peripheral nervous system of intensive care patients. *Neurology.* 2005 Apr. 26; 64(8):1348-53.

Vanhorebeek I, Langouche L, Van den Berghe G. Glycemic and nonglycemic effects of insulin: how do they contribute to a better outcome of critical illness? *Curr Opin Crit Care.* 2005 August; 11(4):304-11.

van den Berghe G, Wouters P, Weekers F, Verwaest C, Bruyninckx F, Schetz M, Vlasselaers D, Ferdinande P, Lauwers P, Bouillon R. Intensive insulin therapy in the critically ill patients. *N Engl J. Med.* 2001 Nov. 8; 345(19):1359-67.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for noninvasive glucose sensing comprising the steps of:
   generating ultrasound pulses or waves using an ultrasound transducer,
   directing the ultrasound pulses or waves into a target tissue,
   detecting reflected, refracted, scattered, back-scattered, or forward-scattered ultrasound pulses or waves from or by boundaries or interfaces in the target tissue using the ultrasound transducer,
   measuring:
      (1) at least one ultrasound time of flight from the detected ultrasound pulses or waves evidencing the boundaries or interfaces within the target tissue using a processor,
      and/or
      (2) at least one ultrasound dimension of a specific tissue layer within the target tissue including thickness, length, width, diameter, curvature, or roughness from the detected ultrasound pulses or waves using the processor; and
   determining a glucose concentration value from:
      (1) the at least one ultrasound time of flight in accordance with an ultrasound time of flight versus glucose calibration curve,
      and/or
      (2) the at least one ultrasound dimension in accordance with an ultrasound dimension versus glucose calibration curve.

2. The method of claim 1, wherein:
   the measuring step comprises measuring:
      (1) at least one ultrasound time of flight from the detected ultrasound pulses or waves evidencing the boundaries or interfaces within the target tissue using a processor,
      and
      (2) at least one ultrasound dimension of the specific tissue layer within the target tissue from the detected ultrasound pulses or waves using the processor, where the ultrasound dimension includes thickness, length, width, diameter, curvature, or roughness, and
   the determining step comprises determining a glucose concentration value from:
      (1) the at least one ultrasound time of flight in accordance with the ultrasound time of flight versus glucose calibration curve,
      and
      (2) the at least one ultrasound dimension in accordance with the ultrasound dimension versus glucose calibration curve.

3. The method of claim 1, further comprising the step of:
   generating electromagnetic pulses or waves using a laser light source,
   directing the electromagnetic pulses or waves into a target tissue,
   detecting reflected, refracted, scattered, back-scattered, or forward-scattered electromagnetic pulses or waves from or by the boundaries or interfaces in target tissue using a photodetector,
   measuring:
      (1) at least one electromagnetic time of flight from the detected electromagnetic pulses or waves evidencing the boundaries or interfaces within the target tissue using the processing unit;
      and/or
      (2) at least one electromagnetic dimension the specific tissue layer within the target tissue from the detected electromagnetic pulses or waves using a photodetector, and
   improving the determining of the glucose concentration value from:
      (1) the at least one electromagnetic time of flight in accordance with an electromagnetic time of flight calibration curve,
      and/or
      (2) the at least one electromagnetic dimension in accordance with an electromagnetic dimension calibration curve,
   where the electromagnetic pulses or waves comprises electromagnetic radiation selected from the group consisting of near infrared, infrared, far infrared, visible, or UV light in the wavelength range from about 200 nanometers to about 100 microns; terahertz waves; microwaves; radiowaves; low-frequency waves; static electric or magnetic fields; or combination of different electromagnetic frequencies.

4. The method of claim 3, wherein
   the second measuring step comprises measuring:
      (1) the at least one electromagnetic time of flight from the detected electromagnetic pulses or waves evidencing the boundaries or interfaces within the target tissue using the processing unit,
      and (2) the at least one electromagnetic dimension of the specific tissue layer within the target tissue from the detected electromagnetic pulses or waves using the processing unit, and improving the determining of the glucose concentration value from:
(1) the at least one electromagnetic time of flight in accordance with the electromagnetic time of flight calibration curve,
and
(2) the at least one electromagnetic dimension in accordance with the electromagnetic dimension calibration curve.

5. The method of claim 3, wherein the electromagnetic pulses are ultrashort in the range from about 1 femtosecond to about 1 microsecond to provide accurate time of flight or dimension measurement.

6. The method of claim 1, further comprising the steps of:
irradiating the target tissue with short optical pulses or waves to generate thermoelastic ultrasound pulses or waves using a laser light source;
detecting reflected, refracted, scattered, back-scattered, or forward-scattered thermoelastic ultrasound pulses or waves from or by using the ultrasound transducer,
measuring:
(1) at least one time of flight from the detected thermoelastic ultrasound pulses or waves evidencing the boundaries or interfaces within the target tissue using the processing unit,
and/or
(2) at least one dimension of the specific tissue layer within the target tissue from the detected thermoelastic ultrasound pulses or waves using the processing unit; and
improving the determining of the glucose concentration value from:
(1) the at least one thermoelastic ultrasound time of flight in accordance with the ultrasound time of flight versus glucose calibration curve,
and/or
(2) the at least one thermoelastic ultrasound dimension in accordance with the ultrasound dimension versus glucose calibration curve.

7. The method of claim 1, further comprising:
measuring an attenuation, a phase, and a frequency spectrum of the detected ultrasound pulses or waves to improve an accuracy and specificity of the glucose concentration value.

8. The method of claim 1, wherein the target tissue comprises a skin tissue, an eye tissue, a mucosal tissue, a nail bed, a lunula, a connective tissue, a muscle tissue, a blood vessel, a cartilage tissue, or a tendon tissue.

9. The method of claim 8, wherein the skin tissue includes a dermis, an epidermis, or subcutaneous fat and the eye tissue includes a lens, an anterior chamber, a vitreous cavity, an eye ball, or a sclera.

10. The method of claim 1, wherein the ultrasound pulses or waves are detected using reflection, focused reflection, refraction, scattering, polarization, confocal, interferometric, low-coherence, or low-coherence interferometry techniques.

11. The method of claim 1, wherein the ultrasound is in the frequency range from about 20 kHz to about 10 Gigahertz with one, two, or multiple frequencies or broad-band ultrasound generated by a piezoelectric element, or by short electromagnetic pulses irradiating a strongly absorbing medium.

12. A system comprising:
an ultrasound source comprising a pulser/receiver and an ultrasound transducer that generates ultrasound pules or waves and directs the ultrasound pulses or waves into a target tissue,
an ultrasound detection subsystem comprising the ultrasound transducer that detects reflected, refracted, scattered, back-scattered, or forward-scattered ultrasound pulses or waves from or by boundaries or interfaces in the target tissue, and
an electronic subsystem comprising a processing unit that:
(1) records and processes the detected ultrasound pulses or waves to determine:
(a) an ultrasound time of flight from the detected ultrasound pulses or waves evidencing the boundaries or interfaces within the target tissue, and/or
(b) at least one ultrasound dimension of a specific tissue layer within the target tissue from the detected ultrasound pulses or waves, and
(2) calculates:
(a) a glucose concentration value from the at least one ultrasound time of flight in accordance with an ultrasound time of flight versus glucose calibration curve, and/or
(b) a glucose concentration value from the at least one ultrasound dimension in accordance with an ultrasound dimension versus glucose calibration curve.

13. The system of claim 12, further comprising:
a display subsystem comprising a display that displays the determined glucose concentration value in electrical communication with the electronic subsystem, where the electrical communication is wireless or non-wireless.

14. The system of claim 12, further comprising:
an electromagnetic source comprising a pulsed laser light source that generates electromagnetic pulses or waves comprising electromagnetic radiation selected from the group consisting of near infrared, infrared, far infrared, visible, or UV light in the wavelength range from about 200 nanometers to about 100 microns; terahertz waves; microwaves; radiowaves; low-frequency waves; static electric or magnetic fields; or combination of different electromagnetic waves,
an electromagnetic delivery subsystem comprising at least one lens that delivers the electromagnetic pulses or waves to the target tissue,
an electromagnetic detection subsystem comprising a photodetector that detects reflected, refracted, scattered, back-scattered, or forward-scattered electromagnetic pulses or waves from, by, or through the target tissue, and
where the electronic subsystem records and processes the detected electromagnetic pulses or waves to determine at least one electromagnetic time of flight and/or at least one electromagnetic dimension from the detected electromagnetic pulses or waves, and improves the calculation of the glucose concentration value from the at least one electromagnetic time of flight or from at least one electromagnetic dimension.

15. The system of claim 14, further comprising:
a display subsystem comprising a display that displays the determined glucose concentration value in electrical communication with the electronic subsystem, where the electrical communication is wireless or non-wireless.

16. The system of claim 14, wherein the electronic subsystem is configured to record and process a combination of ultrasound pulses or waves; a combination of electromagnetic pulses or waves; a combination of ultrasound pulses or waves and electromagnetic pulses or waves; a combination of generated ultrasound pulses or waves and induced ultrasound pulses or waves; a combination of electromagnetic pulses or waves and induced ultrasound pulses or waves; or a combination of ultrasound pulses or waves, electromagnetic pulses or waves, and induced ultrasound pulses or waves.

17. The system of claim 12, wherein the ultrasound pulses or waves have a frequency between about 20 kHz and about 10 Gigahertz.

18. The system of claim 17, wherein the ultrasound pulses or waves comprises two frequencies or multiple frequencies.

19. The system of claim 17, wherein the ultrasound pulses or waves comprise broad-band ultrasound pulses or waves generated by the ultrasound transducer.

20. The system of claim 17, further comprising:
   an electromagnetic source comprising a pulsed laser light source that generates short optical pulses or waves;
   an electromagnetic delivery subsystem comprising at least one lens that delivers the short optical pulses or waves to the target tissue, where the optical pulses or waves generate thermoelastic ultrasound pulses or waves in the target tissue, and
   a thermoelastic ultrasound detection subsystem comprising an ultrasound transducer that detects reflected, refracted, scattered, back-scattered, or forward-scattered thermoelastic ultrasound pulses or waves,
   where the electronic subsystem is further:
      (1) records and processes the detected thermoelastic ultrasound pulses or waves to determine (a) at least one thermoelastic ultrasound time of flight evidencing the boundaries or interfaces within the target tissue from the detected thermoelastic ultrasound pulses or waves, and/or (b) at least one thermoelastic ultrasound dimension of the target tissue from the detected thermoelastic ultrasound pulses or waves, and
      (2) improves the calculation of the glucose concentration value using (1) the at least one thermoelastic ultrasound time of flight, and/or (2) the at least one thermoelastic ultrasound dimension.

21. The system of claim 12, wherein the ultrasound detection subsystem is further configured to detect attenuation, phase, and frequency spectrum of the ultrasound pulses or waves reflected from the target tissue to improve an accuracy and specificity of the glucose concentration value.

22. The system of claim 12, wherein the target tissue comprises a skin tissue, an eye tissue, a mucosal tissue, a nail bed, a lunula, a connective tissue, a muscle tissue, a blood vessel, a cartilage tissue, or a tendon tissue.

23. The system of claim 22, wherein the skin tissue includes a dermis, an epidermis, or subcutaneous fat and the eye tissue includes a lens, an anterior chamber, a vitreous cavity, an eye ball, or a sclera.

* * * * *